United States Patent
Fraas

(10) Patent No.: US 10,814,075 B2
(45) Date of Patent: Oct. 27, 2020

(54) PLUG FOR PLACING ON A CONNECTION ELEMENT OF A MEDICAL SYRINGE

(71) Applicant: Gerresheimer Regensburg GmbH, Regensburg (DE)

(72) Inventor: Andreas Fraas, Amberg (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 131 days.

(21) Appl. No.: 14/871,881

(22) Filed: Sep. 30, 2015

(65) Prior Publication Data
US 2016/0095988 A1 Apr. 7, 2016

(30) Foreign Application Priority Data
Oct. 2, 2014 (DE) .................... 10 2014 114 403

(51) Int. Cl.
*A61M 5/50* (2006.01)
*A61M 5/31* (2006.01)
*A61M 5/34* (2006.01)
*B29L 31/56* (2006.01)
*B29C 45/16* (2006.01)

(52) U.S. Cl.
CPC ............ *A61M 5/5086* (2013.01); *A61M 5/50* (2013.01); *A61M 5/347* (2013.01); *A61M 2005/3104* (2013.01); *A61M 2005/3106* (2013.01); *A61M 2005/3128* (2013.01); *A61M 2205/273* (2013.01); *A61M 2205/276* (2013.01); *B29C 2045/1601* (2013.01); *B29L 2031/565* (2013.01)

(58) Field of Classification Search
CPC .......... A61M 5/437; A61M 2005/3104; A61M 2005/3106
See application file for complete search history.

(56) References Cited

U.S. PATENT DOCUMENTS

| | | | | |
|---|---|---|---|---|
| 4,767,416 A | * | 8/1988 | Wolf | A61M 35/003 128/200.14 |
| 6,112,743 A | * | 9/2000 | Denton | A61M 11/06 128/200.14 |
| 6,231,552 B1 | * | 5/2001 | Jentzen | A61M 5/347 604/187 |
| 6,755,220 B2 | * | 6/2004 | Castellano | A61J 1/2089 141/25 |
| 7,628,781 B2 | | 12/2009 | Roy et al. | |

(Continued)

FOREIGN PATENT DOCUMENTS

| | | |
|---|---|---|
| CA | 2828904 | 7/2012 |
| DE | 20017013 | 1/2001 |

(Continued)

OTHER PUBLICATIONS

Gerresheimer webpage, first posted Sep. 30, 2010, available at http://www.gerresheimer.com/uploads/tx_gerinfo/12_telc_en_01.pdf, 4 pp.

*Primary Examiner* — Manuel A Mendez
*Assistant Examiner* — Courtney B Fredrickson
(74) *Attorney, Agent, or Firm* — Leydig, Voit & Mayer, Ltd.

(57) ABSTRACT

The invention relates to a plug for placing on a connection element (1) of a medical syringe, which is connectable to the connection element (1), the plug (2) comprising a through-duct (3) and being formed free of further connectivity or connection elements.

14 Claims, 3 Drawing Sheets

(56) References Cited

U.S. PATENT DOCUMENTS

Figure 1:
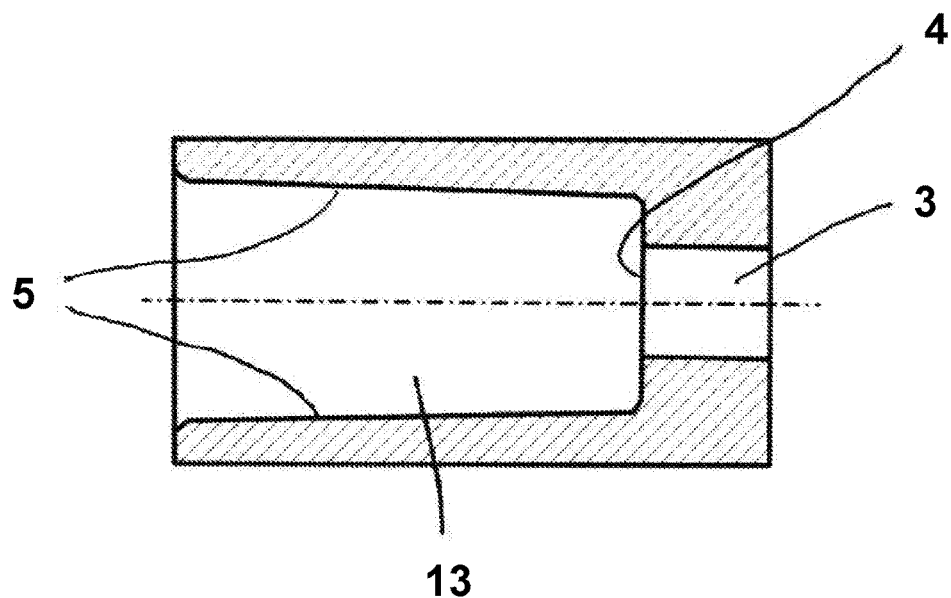

| | | | | |
|---|---|---|---|---|
| 8,864,021 B1* | 10/2014 | Vitello | ............... | A61M 5/5086 235/375 |
| 9,108,031 B2 | 8/2015 | Brandenburger et al. | | |
| 2003/0171721 A1* | 9/2003 | Enomoto | ............ | A61M 5/1408 604/247 |
| 2004/0006312 A1* | 1/2004 | Donnan | .............. | A61M 5/1782 604/181 |
| 2005/0196287 A1* | 9/2005 | Olich | ............... | A61M 5/14216 417/119 |
| 2007/0076401 A1* | 4/2007 | Carrez | ................. | A61M 39/10 361/816 |
| 2007/0190163 A1* | 8/2007 | Malaknov | ............ | A61K 9/0073 424/499 |
| 2008/0275403 A1* | 11/2008 | Maaskamp | ............ | A61M 5/19 604/191 |
| 2009/0099552 A1* | 4/2009 | Levy | ..................... | A61M 39/10 604/533 |
| 2009/0247961 A1* | 10/2009 | Carlyon | ................. | A61M 5/28 604/237 |
| 2011/0028909 A1* | 2/2011 | Lum | ...................... | A61M 5/34 604/192 |
| 2011/0054440 A1 | 3/2011 | Lewis | | |

FOREIGN PATENT DOCUMENTS

| | | |
|---|---|---|
| DE | 10211111552 | 9/2012 |
| EP | 2666513 | 11/2013 |
| IE | 911804 | 1/1992 |
| WO | 2003/076001 | 9/2003 |
| WO | 2010/034470 | 4/2010 |
| WO | 2012/024370 | 2/2012 |

\* cited by examiner

PLUG FOR PLACING ON A CONNECTION ELEMENT OF A MEDICAL SYRINGE

The invention relates to a plug for placing on a connection element of a medical syringe according to the preamble of claim 1.

An example of a plug of this type is the TELC closure originating from the applicant and described in greater detail inter alia on the world wide web at gerresheimer.com/uploads/tx_gerinfo/12_telc_en_01.pdf. This is a tamper-proof syringe closure for screwing on. The invention is based on the fact that normal glass or plastics material syringes are used in various ways in daily operation in a hospital or in a medical facility respectively. In particular for injecting active ingredients, conventional standard syringes comprise a Luer cone and optionally a Luer lock connection. For example, cannulas for intravenous, transcutaneous or subcutaneous injection of active ingredients and pharmaceuticals or nutritional solutions respectively are connected to these standard connection points. However, in this context hose connections or special connectors for connection to a standard syringe via the known Luer systems are also conceivable. In normal hospital operation, standard syringes of this type are used primarily because of the ready availability, but are also used for withdrawing, measuring out and even orally or dermally applying active ingredients.

From cited document DE 10 2011 111 552 A1 a syringe with a closure is known. The closure comprises a closure cap which closes the needle lip part of the syringe in a sealing manner and a securing cap which grips the closure cap and fastens the same to the needle lip part via a holding ring. Furthermore, the securing cap and the closure cap are formed in one part.

Furthermore, from cited document DE 200 17 013 U1 a closure body for a Luer lock connection is known. The closure body comprises a cap which overlaps the Luer cone. At the outer side of the cap a Luer lock thread is provided. The interior of the cap is formed in a conical shape so that it applies to the Luer cone, wherein the inner cone of the cap extends via less than half the length of the Luer cone.

However, this general use of standard syringes also involves significant risks. Thus, it repeatedly happens that, through carelessness, a change in responsibilities or similar circumstances, a syringe prepared for oral or dermal administration is administered intravenously, transcutaneously or subcutaneously. A use of this type for an unintended purpose also occurs in particular because the provided Luer systems make it tempting to connect a cannula. To draw an active ingredient, a pharmaceutical or a nutritional solution into a syringe of this type, the protector or closure respectively has first to be removed from the syringe. After this closure is removed, it is possible to draw the active ingredient, the pharmaceutical or the nutritional solution into the syringe body. After the syringe is prepared, the closure is not replaced in normal operation, since it would have to be removed again for example for oral administration. In addition, there is again the risk that the syringe may be equipped with a cannula after the closure is removed again. In the recent past, such incorrect uses of syringes with active ingredients, pharmaceuticals or nutritional solutions already drawn in have led to incidents with in some cases lethal consequences for the patients.

Therefore, the object of the invention is to develop a plug for placing on a connection means of a medical syringe in such a way that incidents of this type with in some cases lethal consequences for the patients can be prevented.

This object is achieved by a plug for placing on a connection element of a medical syringe having all of the features of claim 1. Advantageous embodiments of the invention may be found in the dependent claims.

The plug according to the invention for placing on a connection element of a medical syringe which is connectable to the connection element is characterized in that the plug comprises a through-duct and is formed free of further connectivity or connection elements. A plug of this type according to the invention is thus formed to be compatible with common syringe connections, in such a way that, after it is attached to or placed respectively on the syringe, the application of a different application element, such as a hose, a cannula or a catheter, is prevented. However, to make the planned oral or dermal application still possible, unlike the closures known in the art, the plug comprises an opening through which the active ingredient, pharmaceutical or nutritional solution received in the syringe respectively can be applied in the mouth or on the skin of the patient. In this context, a plug of this type refers to any placed-on element which can be placed on the connection element in a manner corresponding to a closure, such as the aforementioned TELC closure, and in which a medium received in the syringe can be applied orally or dermally through the through-duct. The fact that the plug is formed free of further connectivity or connection elements also prevents further application devices for intravenous, transcutaneous or subcutaneous injection of active ingredients and pharmaceuticals or nutritional solutions, such as cannulas, catheters or the like, from being connected thereto.

The use of the plug according to the invention therefore reliably prevents a syringe prepared for oral or dermal application from being used in another manner, in particular for intravenous, transcutaneous or subcutaneous injection of active ingredients and pharmaceuticals or nutritional solutions, since it is no longer possible to connect any further connection or application element respectively, in particular a cannula, catheter or hose, to the plug according to the invention. According to the invention, this effectively prevents incorrect intravenous, transcutaneous and/or subcutaneous applications.

In a first advantageous embodiment of the invention, the plug is therefore formed for oral and/or dermal application of a medium.

In a particularly advantageous embodiment of the invention, the plug comprises an inner cone of a Luer cone, which is formed to cooperate with an outer cone of a Luer cone of a medical syringe. Since standardised syringes comprising Luer cones of this type are used in hospitals and similar medical facilities, it has been found to be advantageous to form the plugs according to the invention in such a way that they are connectable to the standardised syringes.

In the same way, it has likewise been found to be advantageous for the plug to comprise an external thread of a Luer lock connection, which is formed to cooperate with an internal thread of a Luer lock connection of a medical syringe. It is thus also possible in a simple manner to connect the plug according to the invention to standardised syringes comprising Luer lock systems.

In a particularly advantageous embodiment of the invention, the plug is formed to be placed irreversibly on a medical syringe. This ensures that once a plug has been placed on the syringe it can no longer be removed therefrom. This is advantageous in particular because even deliberate intravenous application of an active ingredient provided for oral or dermal application and received in the syringe is prevented. Specifically, the plug according to the invention can no longer be removed, and so no other connection or application element respectively in the form of a cannula, catheter or hose connection can be connected thereto.

In this context, in another embodiment of the invention, the plug comprises a first portion and a second portion which is releasably connected to the first portion via at least one predetermined breaking point. This means that, in particular if Luer lock systems are used, the second portion can be released from the first portion by way of the predetermined breaking points if rotated further, meaning that the first portion as a male part is received or depressed into the connection element, formed as a female part of the Luer lock system, of the medical syringe, in such a way that no part of the counter element protrudes from this connection element. There is thus no weak point for releasing the counter element from the connection element. This further increases safety against the possibility of intravenous injection of the medium drawn into the syringe and provided for oral or dermal application, since no other connection or application element respectively, such as for example a cannula, catheter or hose element, can be connected thereto. However, according to the invention, the use of predetermined breaking points of this type is not limited to Luer lock systems, but can also be used with other connection types such as Luer slip systems or completely different connection types.

Alternatively, it is naturally also possible to implement an irreversible arrangement of this type of a plug according to the invention on a syringe in a different manner. For example, it should be noted that, in Luer lock systems, the external thread of the counter element for example comprises barb-like elements which prevent the plug according to the invention from being unscrewed in that these barb-like elements fix themselves in the internal thread of the Luer lock element of the syringe. Naturally, other geometries which would make unscrewing impossible are also conceivable in the thread pitch. In the case of a Luer slip system, the Luer cone connection could have a correspondingly tight fit. Irrespective of the system, latch and counter latch elements or clip and counter clip elements could be provided.

A further embodiment of the invention provides that at least one marking element is provided which labels a medical syringe, provided with the plug according to the invention, for oral or dermal application. Marking elements of this type may be arranged in various ways. In one embodiment, this may be a written indication that the syringe provided with a plug according to the invention may only be used for oral or dermal application. Alternatively, the marking element may also be a region of the plug according to the invention which is provided with a signal colour. Corresponding combinations of different marking elements are also conceivable.

To provide economically effective, cost-efficient production of the plug according to the invention, it has been found expedient for the plug to consist at least in part of a plastics material, for example a thermoplastic elastomer, of rubber or of silicone. Production using materials of this type is very simple in terms of the process and has also been found to be expedient for medical technology as a whole.

In this context, a further embodiment of the invention provides that the through-duct of the plug according to the invention can be closed by means of a sealing element. This means that the contents of a syringe prepared for oral application and provided with a plug of this type cannot be contaminated through the through-duct after the active ingredient, pharmaceutical or nutritional solution is drawn in. The sealing element reliably seals the contents of the syringe against the environment. This prevents contamination.

Advantageously, the sealing element is formed as a valve or the like, in particular as a non-return valve, ball non-return valve, poppet non-return valve, non-return flap or the like. Valves of this type have the advantage that they are only permeable to media in one direction. After the syringe has been prepared for oral or dermal application and closed using the plug according to the invention, it is subsequently no longer possible to draw further media into the syringe, since the described valves no longer allow medium through in the direction towards the syringe contents. However, after the actuation of the syringe piston, the syringe contents are driven out of the syringe chamber through the through-duct, the described valves now being permeable to the medium in this direction.

Further aims, advantages, features and possible applications of the present invention may be taken from the following description of embodiments with reference to the drawings. In this respect, all of the features described and/or shown in the drawings, individually or in any reasonable combination, form the subject matter of the invention, also regardless of how they are combined in the claims or the dependencies thereof.

Figure 2:
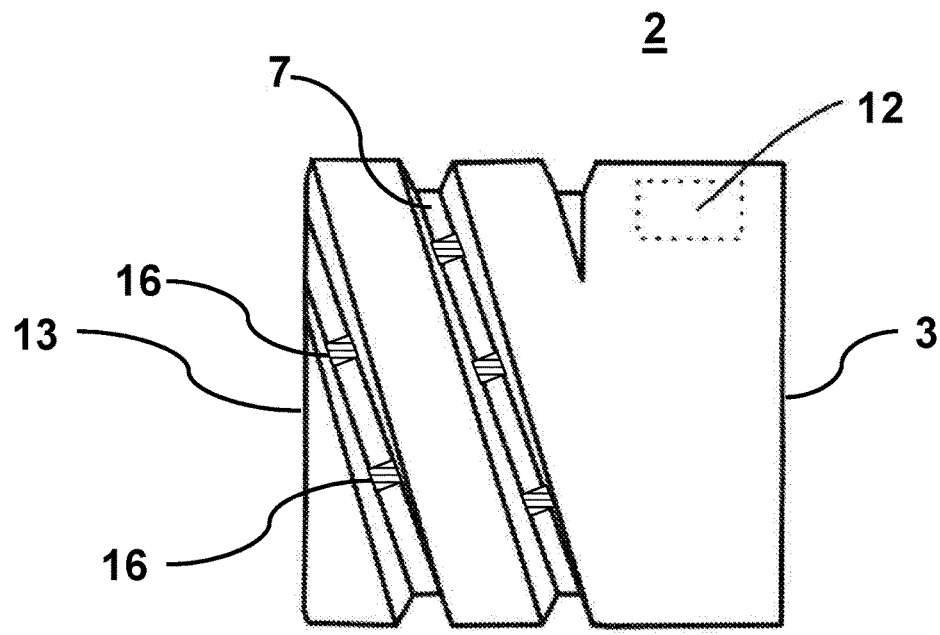
Figure 3:
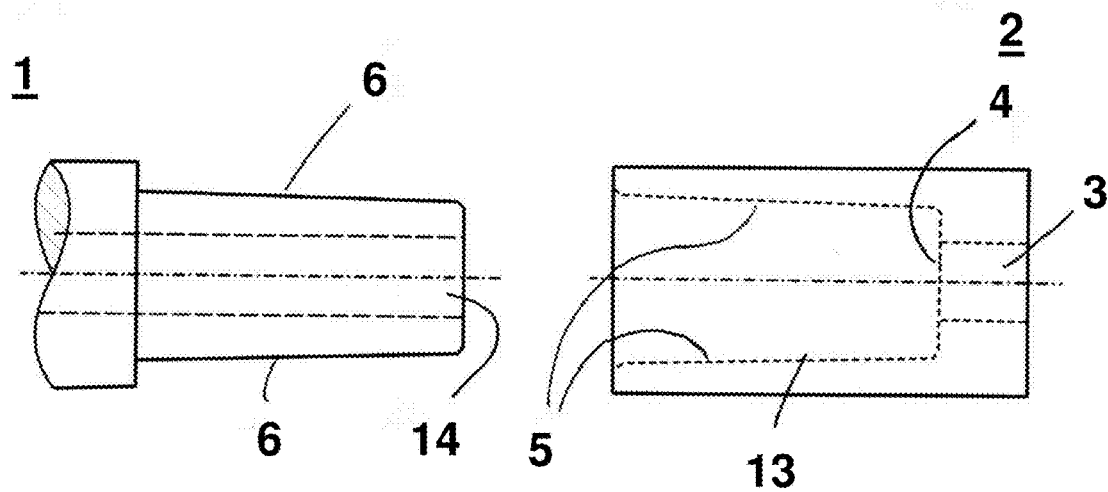
Figure 4:
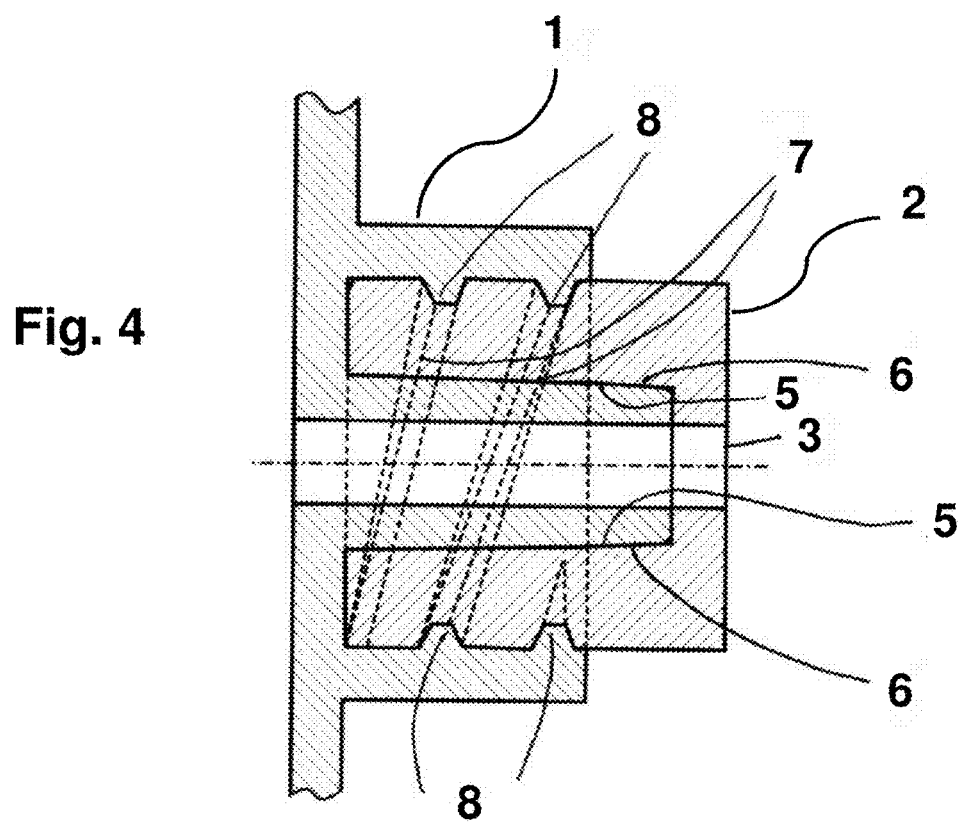
Figure 5:
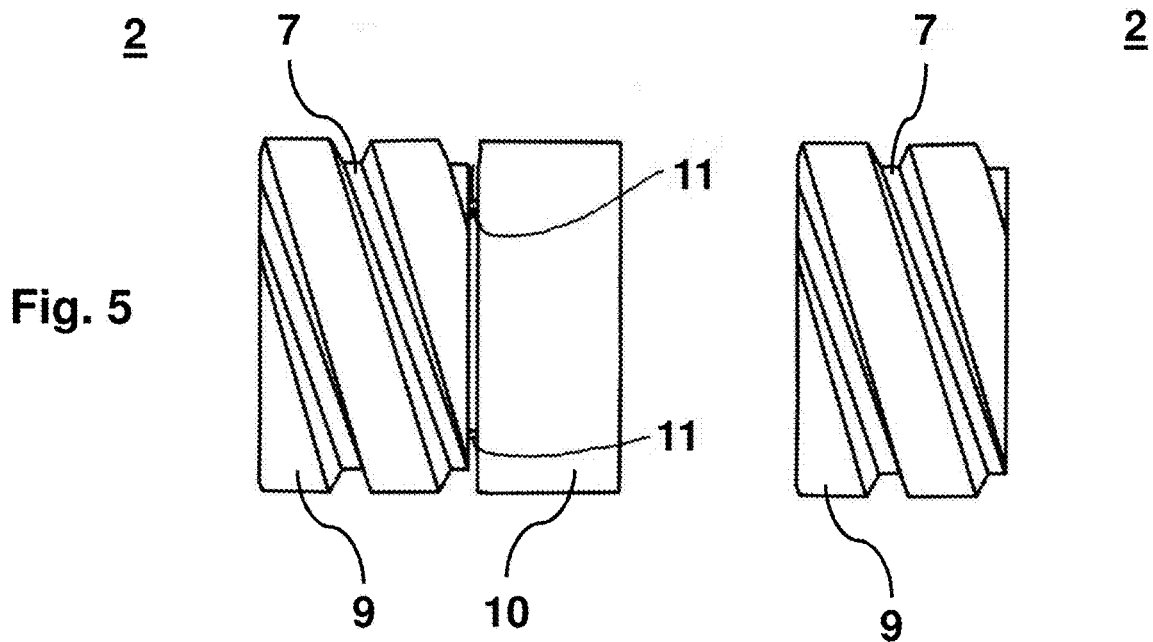
Figure 6:
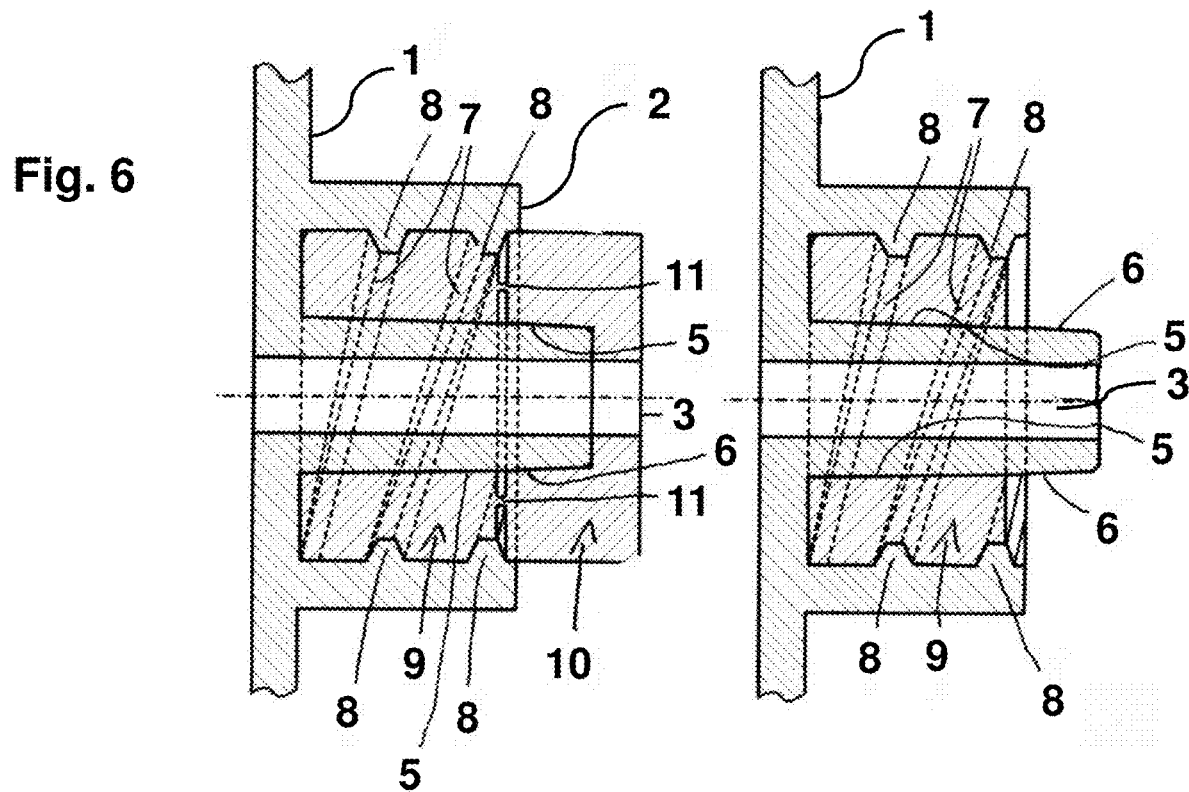

In the drawings:

FIG. 1 is a cross-sectional drawing of a first embodiment of a plug according to the invention, FIG. 2 is a cross-sectional drawing of a second embodiment of a plug according to the invention, FIG. 3 is a plan view of the embodiment of FIG. 1 along with a corresponding Luer connection, FIG. 4 is a cross-sectional drawing of the embodiment of FIG. 2 along with a corresponding Luer lock connection, FIG. 5 shows a third embodiment of a plug according to the invention in two different states, FIG. 6 is a cross-sectional drawing of the embodiment of FIG. 5 along with a corresponding Luer lock connection in two different states.

FIG. 1 is a cross-sectional drawing of a first embodiment of a plug 2 according to the invention. In this respect, the plug 2 comprises an inner cone 5 which forms a cavity 13. In this respect, the inner cone 5 extends conically from left to right, in such a way that the cavity 13 tapers to the right. The cavity 13 is connected to a through-duct 3, in such a way that a medium can pass through the plug 2 in an unimpeded manner.

To make it only possible for a medium to pass through the plug 2 in one direction, a sealing element 15 may be provided and is advantageously formed as a non-return valve, ball non-return valve, poppet non-return valve, non-return flap or the like.

In an embodiment not shown here, latch or clip elements are further formed on the plug 2. These can cooperate with counter latch or counter clip elements of a connection element 1 of a syringe respectively in such a way that the plug 2 can be fastened unreleasably and irreversibly to a connection element 1 of a syringe.

In a further embodiment (not shown here), barb-like elements may be provided in a Luer lock system in an external thread 7 of the plug 2. These barb-like elements likewise prevent a plug 2 from being released again once it has been placed on a syringe.

FIG. 3 shows a connection element 1 of this type. As can be seen, this connection element 1 comprises an outer cone 6 and a medium duct 14. As can also be seen from FIG. 3, the outer cone 6 of the connection element 1 and the inner cone 5 of the counter element 2 are formed as a unitary Luer slip system, in such a way that the inner cone 5 of the counter element 2 as a female part of this system receives the outer cone 6 of the connection element 1 as a male part, and a connection between the connection element 1 and the plug 2 is thus provided.

FIG. 2 now is a plan view of another embodiment of a plug 2 according to the invention. In this respect, it can be seen that the plug 2 therein is cylindrical in form and is provided with an external thread 7. Further, a marking element 12 can be seen clearly in FIG. 2. This marking element 12 serves to label a medical syringe, provided with a plug 2, for oral or dermal application respectively. Marking elements 12 of this type may in this respect be arranged in various ways. In one embodiment, this may be a written indication that the syringe provided with a plug 2 according to the invention may only be used for oral or dermal application respectively. Alternatively, the marking element 12 may also be a region of the plug 2 according to the invention which is provided with a signal colour, it naturally also being possible to provide the entire plug 2 with this signal colour. Corresponding combinations of different marking elements 12 are also conceivable.

In FIG. 4, the external thread 7 of the plug 2 according to the invention of FIG. 2 is now screwed into an internal thread 8 of a connection element 1. The system therein thus forms a Luer lock system. In this case too, the plug 2 is formed with a cavity 13, as shown in FIG. 2 but not provided with this reference numeral in FIG. 4 for reasons of clarity, which is connected to a through-duct 3 in a manner corresponding to the cavity 13 of the embodiment of FIG. 1. The connection between the connection element 1 and the plug 2 is in this respect implemented in a manner analogous to the embodiment of FIGS. 1 and 3, the internal thread 8 and the internal thread 7 resulting in exact guidance, as is conventional in Luer lock systems. The marking field 12 now displays to the user that a syringe provided with a plug of this type can no longer be provided with or connected respectively to another coupling element, such for example as a cannula or a hose system, and may only be used for oral or dermal application respectively.

In this embodiment too, although this is not shown, it may be provided for the connection of the connection element and the plug 2 to be irreversible. In this case too, this irreversibility may be achieved in that latch or clip elements 16 are further attached to the counter element 2. These may cooperate with counter latch or counter clip elements of a connection element 1 of a syringe respectively in such a way that the plug 2 can be fastened unreleasably and irreversibly to a connection element 1 of a syringe.

Alternatively, it may naturally also be provided that the external thread 7 of the plug 2 comprises barb-like elements 16 which prevent the plug 2 according to the invention from unscrewing in that these barb-like elements fix themselves in the internal thread 8 of the Luer lock element of the syringe or of the connection element 1 respectively.

Finally, FIGS. 5 and 6 show a third embodiment of a plug 2 according to the invention, the basic functionality of which corresponds to the embodiment of FIGS. 2 and 4. The basic difference from the embodiment of FIGS. 2 and 4 is that the plug 2 comprises a first portion 9 and a second portion 10 which are interconnected via at least one predetermined breaking point 11.

In this case, it may be provided that there is exactly one predetermined breaking point 11, which annularly encloses the counter element 2 and is formed as a material weak point. Alternatively, a plurality of predetermined breaking points 11 may be provided, for example in the form of webs.

Using the plug 2 of the embodiment of FIGS. 5 and 6, it is also possible to ensure that a syringe provided with a plug 2 of this type can no longer be used for intravenous, transcutaneous or subcutaneous application. Before being placed on a syringe, the plug 2 according to the invention of this embodiment has the shape shown in the left-hand drawing of FIG. 5. The external thread 7 of this plug 2 is subsequently screwed into the internal thread 8 of the connection element until the outer cone 6 of the connection element 1 comes to be positioned against the inner cone 5 of the plug 2. This arrangement is shown in the left-hand drawing of FIG. 6. The connection element 1 and the plug 2 are thus now interconnected.

To prevent the possibility of the plug 2 simply being screwed out of the connection element 1 of the syringe again and a cannula or the like being connected to the connection element 1 or the syringe, the plug 2 is rotated further in a closing direction in a simple manner. This breaks the predetermined breaking point(s) 11, in such a way that the second portion 10 of the plug 2 is released from the first portion 9 of the plug 2.

As can be seen from the right-hand drawing of FIG. 6, in this respect, the first portion 9 of the plug 2 is now received in the connection element 1 between the internal thread 8 and the outer cone 6 thereof in such a way that no part of the first portion 9 of the plug 2 protrudes there. Thus, there is also no possibility of screwing this first portion 9 of the plug back out of the connection element 1 of the syringe. This ensures that a syringe provided with a plug 2 of this type is not usable for intravenous, transcutaneous or subcutaneous application, and that it is no longer possible to connect a cannula, catheter or the like to the connection element 1.

As can be seen in particular from the right-hand drawing of FIG. 6, the element 9 of the plug 2 remaining on the syringe is arranged on the syringe in such a way that it generally does not come into contact with the medium for application during oral or dermal application respectively. During correct use, in this respect, the medium only comes into contact with a medium duct, as shown in FIGS. 4 and 6, arranged in the connection element 1.

LIST OF REFERENCE NUMERALS 1 connection element
2 plug
3 through-duct
5 inner cone
6 outer cone
7 external thread
8 internal thread
9 first portion
10 second portion
11 predetermined breaking point
12 marking element
13 cavity
14 medium duct
15 sealing element
16 latch, clip or barb-like elements

The invention claimed is:

1. A Luer lock system comprising a connection element of a medical syringe and a plug connected to said connection element,
   said connection element comprising an outer cone, an internal thread of the Luer lock, and a medium duct, and said plug comprising a first end and a second end, an external thread of the Luer lock extending from the first end toward the second end, a through-duct extending from the second end toward the first end, and an inner cone of a Luer cone extending from the first end toward the second end, said inner cone forming a tapered cavity connected to the through-duct, wherein the second end is a flat surface, wherein said external thread is screwed into the internal thread of said connection element such that the majority of the plug is positioned within the connection element, and the outer cone of the connection element is positioned within the inner cone of the plug so that a medium is able to pass through the medium duct to the through-duct;

wherein said plug is not coupled to a hose, cannula or catheter; and wherein said through-duct is proximate to said external thread of said Luer lock, and a diameter of the tapered cavity is greater than a diameter of the through-duct where the tapered cavity connects with the through-duct.

2. The Luer lock system according to claim 1, wherein said plug comprises latch or clip elements which cooperate with counter latch or counter clip elements of the connection element in such a way that the plug can be attached to the connection element in an irreversible manner.

3. The Luer lock system according to claim 1, wherein said plug comprises barb-like elements by means of which the plug can be attached to the connection element in an irreversible manner.

4. The Luer lock system according to claim 1, wherein said plug comprises a first portion and a second portion, and said second portion is connected to the first portion in a releasable manner by means of at least one predetermined breaking point.

5. The Luer lock system according to claim 4, wherein said at least one predetermined breaking point is in the form of a web.

6. The Luer lock system according to claim 5, wherein said first portion is formed in such a way that it is complete received in and/or depressed into said connection element when said plug is connected to said syringe.

7. The Luer lock system according to claim 4, wherein said first portion is formed in such a way that it is completely received in and/or depressed into the connection element when the plug is connected to the syringe.

8. The Luer lock system according to claim 1 further comprising at least one marking element, wherein said at least one marking element labels said medical syringe provided with the plug for a particular type of application.

9. The Luer lock system according to claim 1, wherein said plug comprises at least in part a plastic material.

10. The Luer lock system according to claim 1, further comprising a sealing element formed as a valve, configured so that the medium can only pass through the through-duct in a direction out of the medical syringe.

11. The Luer lock system according to claim 10, wherein said valve is a ball non-return valve, a poppet non-return valve, or a non-return flap.

12. The Luer lock system according to claim 1, wherein said plug comprises at least in part a thermoplastic elastomer, a rubber, a silicon or a combination thereof.

13. The Luer lock system according to claim 1, wherein the lack of hose, cannula or catheter prevents intravenous, transcutaneous or subcutaneous applications.

14. A Luer lock system comprising a connection element of a medical syringe and a plug connected to said connection element, said connection element comprising an outer cone, an internal thread of the Luer lock, and a medium duct, and said plug comprising a first end and a second end, an external thread of the Luer lock extending from the first end toward the second end, a through-duct extending from the second end toward the first end, and an inner cone of a Luer cone extending from the first end toward the second end, said inner cone forming a tapered cavity connected to the through-duct, wherein the second end is a flat surface, wherein said external thread is screwed into the internal thread of said connection element such that the majority of the plug is positioned within the connection element, and the outer cone of the connection element is positioned within the inner cone of the plug so that a medium is able to pass through the medium duct to the through-duct;

wherein said plug is free of an internal thread of a Luer lock, an outer cone of a Luer cone or any combination thereof;

wherein said plug is not coupled to a hose, cannula or catheter; and wherein said through-duct is proximate to said external thread of said Luer lock, and a diameter of the tapered cavity is greater than a diameter of the through-duct where the tapered cavity connects with the through-duct.

* * * * *